United States Patent [19]
Andrews et al.

[11] Patent Number: 5,929,453
[45] Date of Patent: Jul. 27, 1999

[54] UNDERWATER SPECTROSCOPIC DETECTOR

[75] Inventors: John M. Andrews; Leonard J. Martini, both of San Diego; Stephen H. Lieberman, La Mesa; Leon V. Smith; Gregory W. Anderson, both of San Diego, all of Calif.

[73] Assignee: The United States of America as represented by the Secretary of the Navy, Washington, D.C.

[21] Appl. No.: 08/868,114

[22] Filed: Jun. 3, 1997

[51] Int. Cl.$^6$ .................................................. G01N 21/64
[52] U.S. Cl. ........................................................ 250/461.1
[58] Field of Search ................................. 356/317, 318, 356/417, 73, 70; 250/461.1, 461.2, 458.1, 459.1

[56] References Cited

U.S. PATENT DOCUMENTS

| | | |
|---|---|---|
| 4,434,364 | 2/1984 | Correa et al. . |
| 4,730,922 | 3/1988 | Bach et al. . |
| 4,942,303 | 7/1990 | Kolber et al. ............................ 356/417 |
| 5,308,505 | 5/1994 | Titus et al. . |
| 5,322,569 | 6/1994 | Titus et al. . |
| 5,449,625 | 9/1995 | Kobayashi et al. . |
| 5,578,818 | 11/1996 | Kain et al. . |
| 5,604,582 | 2/1997 | Rhoads et al. ........................... 306/417 |

OTHER PUBLICATIONS

Spectrogram Corporation Brochure: OSPRA™ Oil Spill Remote Alarm System No date known.
Sweedler et al "High . . . Detectors"; Analytical Chemistry, vol. 60, No. 4 Feb. 15, 1988 pp. 282–291.

*Primary Examiner*—K P Hantis
*Attorney, Agent, or Firm*—Harvey Fendelman; Peter A. Lipovsky; Michael A. Kagan

[57] ABSTRACT

A spectroscopic detector suitable for detecting oil spills in an aquatic environment includes a buoyant container having an optical window; an optical energy generator mounted in the container for directing an optical energy beam through the window; an optical detector for generating an output signal in response to detecting a second optical energy beam received in the container through the window; and a beam splitter for directing the second optical energy beam to the optical detector. The generation of the optical energy beam and operation of the optical detector may be time gated to reduce thermal noise and isolate the sampled optical energy from background light. The optical energy beam preferably has UV components which inhibits the formation of biological organisms on the optical window.

25 Claims, 8 Drawing Sheets

UNDERWATER SPECTROSCOPIC DETECTOR

BACKGROUND OF THE INVENTION

The present invention generally relates to the field of spectroscopy, and more particularly, to an underwater spectroscopic detector for detecting substances in aqueous solutions.

Current Navy practices for detecting petroleum spills at marine facilities rely solely upon human visual observation to identify the surface sheen caused by oil floating on water. The problem with the practice is that visual observation provides only a limited and often unreliable means of detecting spilled fuel or oil. Many spills occur at places or times in which no one is present to discover the event. Even when an observer is present, visual spill sighting is difficult during foul weather and is completely ineffective at night. Prompt containment of oil spills is important in order to minimize the difficulty and environmental damage caused by such spills. Therefore, a need exists for a reliable system that can promptly detect an oil spill.

One type of oil spill detector employs fluorometric sensors mounted above the water surface on a free floating buoy platform. When an oil spill is detected, the sensors generate a signal that triggers an alarm. Because the detector floats on the surface of the marine environment, the optical energy generator used to stimulate fluorescent of the oil particles and the attendant electronics are encased in an explosion proof housing to eliminate the risk of explosion that would occur if explosive volatile components, such as are found in oil, should ever penetrate the detector. However, explosion proof housings are expensive and heavy. Further, this type of detector can detect surface contaminants, but not dissolved or emulsified petroleum products.

A problem with present underwater instruments in general is that optical elements exposed to marine environments tend to become fouled with biological organisms within mere days of deployment. Continued service of such detectors requires that they be periodically cleaned, an expensive and time consuming process which renders them unsuitable for extended deployments particularly in remote locations.

Therefore, a need exists for an oil spill sensor that avoids the risk of explosion and eliminates the need for an explosion proof housing. A need also exists for a detector that can detect contaminants within a water column, as well as on the surface of an aquatic body. A further need exists for an oil spill sensor that can be operated underwater for extended periods without becoming fouled with biological organisms.

SUMMARY OF THE INVENTION

The present invention provides a spectroscopic detector suitable for detecting oil spills in an aqueous environment and includes a structure having an optical window; an optical energy generator supported by the structure for directing an optical energy beam through the window; an optical detector for generating an output signal in response to detecting a second optical energy beam received in the container through the window; and a beam splitter for directing the second optical energy beam to the optical detector. The generation of the optical energy beam and operation of the optical detector may be modulated to reduce thermal noise while minimizing the influence of background light on the output of the detector. The optical energy beam preferably has UV components which inhibit the formation of biological organisms on the optical window.

BRIEF DESCRIPTION OF THE DRAWINGS

Throughout the several views, like elements are referenced using like references.

DESCRIPTION OF THE PREFERRED EMBODIMENT

Figure 1:
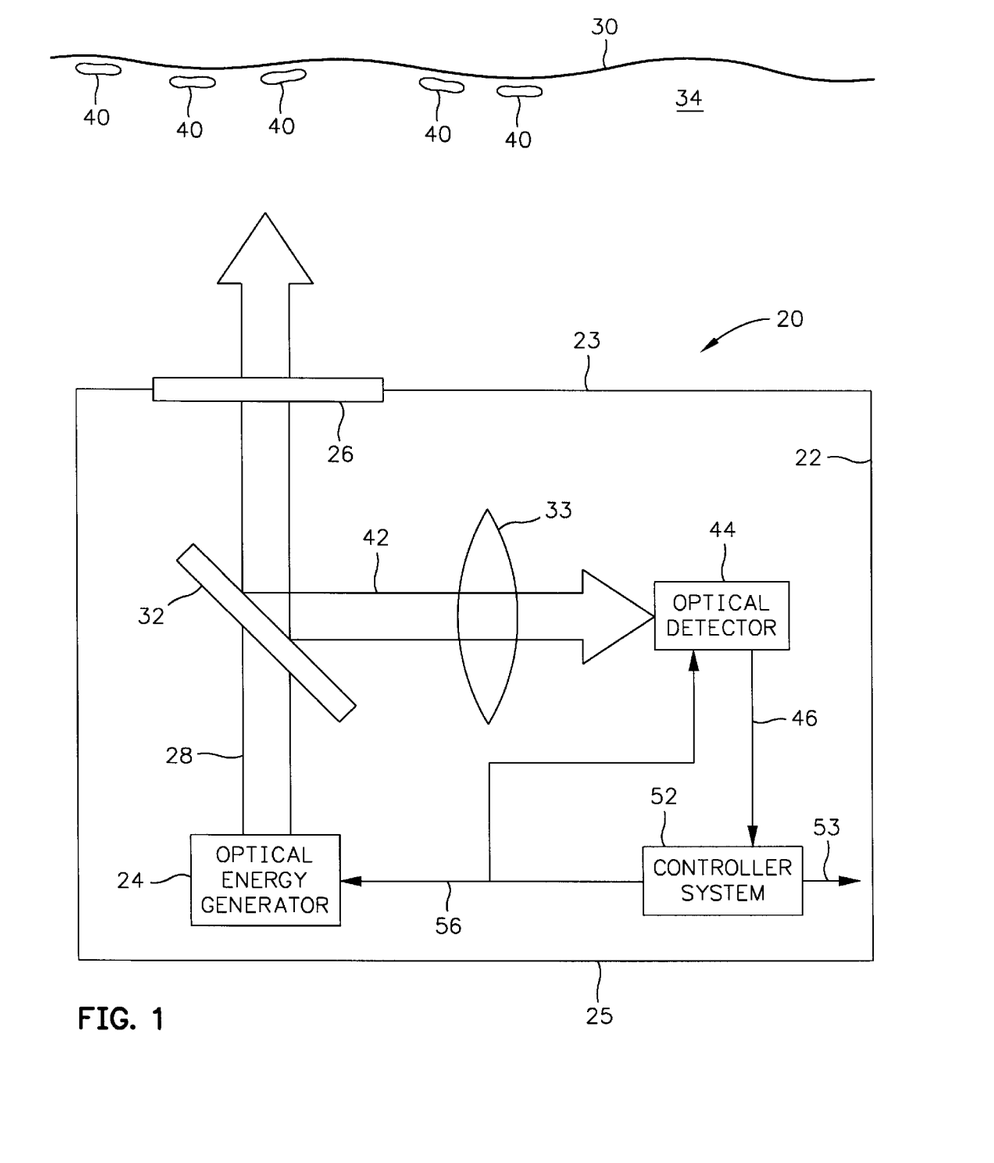
FIG. 1 is a block diagram of an underwater spectroscopic detector embodying various features of the present invention.
Figure 2:
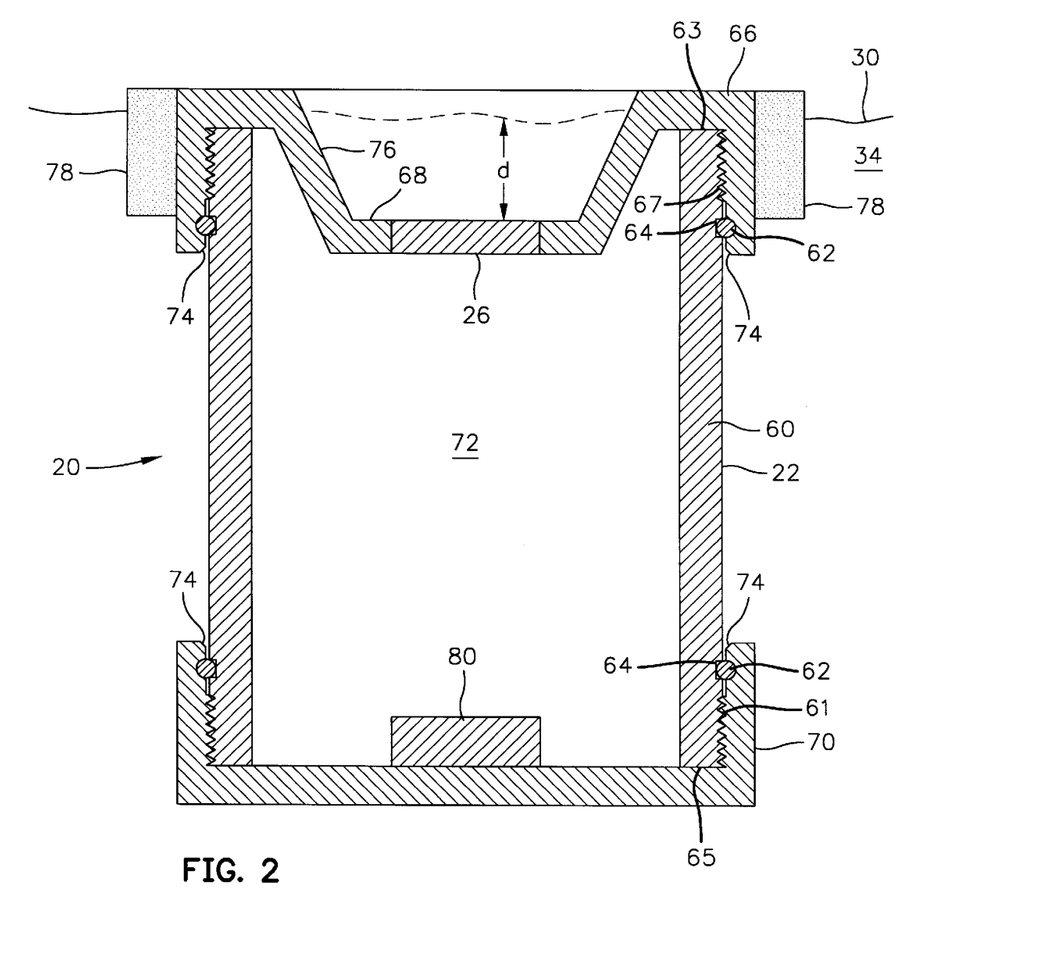
FIG. 2 is a cross-sectional view of an example of a waterproof container in which the underwater spectroscopic detector may be mounted.

Referring now to FIG. 1, there is shown an underwater spectroscopic detector 20 suitable for detecting oil and other types of chemicals present in aquatic environments, such as sea water or fresh water lakes. The detector 20 is preferably encased in a waterproof container, or structure 22 having an optically transparent window 26 so that window 26 is positioned below the surface 30 of aquatic environment 34. The structure may have positive, neutral, or negative buoyancy, as required to suit the requirements of a particular application. However, structure 22 is shown in FIG. 2 and described herein as having, by way of example, positive buoyancy. The structure 22 may be made from a polypropylene tube capped at each of ends 23 and 25. The detector 20 includes an optical energy generator 24 mounted in structure 22 which generates an excitation optical beam 28, which includes ultraviolet light (UV) components characterized by wavelengths less than about 315 nm, that is directed through a beam splitter 32. Beam splitter 32 is preferably transparent to light having wave-length components less than about 315 nm and is transected by excitation optical beam 28. After passing through the beam splitter 32, excitation optical beam 28 is directed out of the structure 22 through the window 26 into the surrounding aqueous environment 34. Chemical species 40 of interest present in aqueous environment 34 generally fluoresce when irradiated by the UV light components comprising excitation optical beam 28. The fluorescing chemical species thereby generate fluorescing optical beam 42 having light components with wave-lengths greater than those of the excitation optical energy beam 28. The light beam 42 generated in the aqueous environment 34 enters structure 22 through window 26 and is reflected by beam splitter 32 to optical detector 44. The optical detector 44 generates an output signal 46 indicating detection of the chemical species 40. By way of example, the beam splitter 32 may be a dichroic mirror. In the preferred embodiment, the spectroscopic detector 20 preferably further includes a controller 52 which: 1) generates control signals 56 that direct optical energy generator 24 to generate optical beam 28 as a pulsed beam at a frequency, for example, of 30 Hz and having a pulse period of about 200 $\mu$s; and 2) synchronizes the optical detector 44 to integrate the intensity of detect light beam 42 only during the pulse period of optical beam 28. The generation of optical beam 28 and detection of optical beam 42 by optical detector 44 are synchronized in unison, or time gated (modulated) to isolate the signal of interest (optical beam 42) from background light, such as sunlight, and to minimize thermal noise. The controller 52 may also store and/or process output signal 46 that represents the integrated intensity of optical beam 42. The output signal 46 may be subjected to further data processing or used as a control signal.

In the preferred embodiment, optical generator 24 may typically generate optical energy having wavelengths in the range of about 150 to 400 nanometers. By way of example, optical generator 24 include a may be a pulsed xenon flashlamp to induce fluorescence in chemical species 40 which are expected to consist essentially of aromatic components of free phase, dissolved phase and emulsified petroleum hydrocarbon contamination in the aquatic environment 34. A xenon flashlamp generates broadband optical energy including optical energy having ultraviolet light components (wavelengths <315 nm). Ultraviolet light has sufficient energy so that irradiation of window 26 with optical beam 28 inhibits, and in many cases prevents, the accumulation of biological organisms on the window 26, which would otherwise become fouled with biological organisms soon after deployment of spectroscopic detector 20 in an aquatic environment. The window 26 is preferably made of an optically transparent material such as quartz, glass, or sapphire, and may be lens shaped to focus optical beams 28 and 42. Detector 20 may further include a lens 33 to focus optical beam 42 onto optical detector 44.

Alternatively, optical generator 24 may also include an Hg lamp, deuterium lamp, a UV laser such as XeCl, $N_2$, or a frequency doubled (or quadrupled) visible laser. The optical detector 44 may include a photo diode array, CCD camera, or photo multiplier tube. However, the detector 20 may also be used to detect other types of chemical species as well, and its application is not limited merely to detecting aromatic compounds.

Fluorescence provides an extremely sensitive method for accurately quantifying trace levels of hydrocarbons present in an aquatic environment. Spectral analysis provides discrimination between various classes of hydrocarbons and minimizes interference due to non-hydrocarbon fluorescence. An important advantage of the sensor 20 is the one-window design uses the ultraviolet light components generated by the optical generator 24 to inhibit or prevent biological fouling on the optical window 26.

Waterproof structure 22 may be constructed as shown in FIG. 2 to include a tube 60 having threaded regions 61 at each of ends 63 and 65, between which are located grooves 64 in which O-rings 62 are fitted. A conventional end cap 70 is threaded to the lower end 65 of structure 22 whereupon the bottom O-ring 62 provides a watertight seal to prevent water from entering the interior 72 of the structure 22. An upper cap 66 is screwed to the threaded region 61 at the upper end 63 of the tube 60 structure 22 so that the cap 66 fits over and compresses the upper O-ring 62 to provide a watertight seal between the aquatic environment 34 and the interior 72 of structure 22. The upper cap has a recessed region 76 into which is mounted optically transparent window 26. The recessed region 76 allows the structure 22 to float at the surface 30 of the aquatic environment 34 so that window 26 is positioned preferably just below the surface 30 by a distance d, thereby coupling the window to the surface 30. By way of example, d is preferably less than about 10 cm. The inside edges 74 of the end caps 70 and 66 may be chamfered to avoid damaging O-rings 62 when the caps 66 and 70 are fitted over them. Air within the structure 22 provides the detector 20 with positive buoyancy. However, there may be some applications where it may be desirable to provide detector 20 with additional buoyancy, as for example, by mounting an annularly shaped buoyant structure 78 formed of closed cell foam to the upper end of cap 66 of structure 22. Attachment of a ballast weight 80 at the bottom of the structure 22, as for example, to the interior surface of cap 70, may be necessary to assure that window 26 floats just beneath the surface 30 of the aquatic environment 34.

An important advantage of the detector 20 is that underwater positioning of the electronics which drive the detector 20 preclude the explosion hazard that would otherwise result from electronics in the presence of volatile petroleum products that the detector is designed to detect.

Another embodiment of an underwater spectroscopic detector 100 embodying various features of the present invention is described with reference to FIG. 3. The detector 100 is mounted in a waterproof container 101 and includes an optically transparent window 103 through which optical energy may be propagated between the interior and exterior of the container 101. The window 103 is mounted in a recessed aperture 109 formed in the top 111 of the container 101. A buoyant structure 105 mounted to the top of the container 101, weight 107 mounted to the bottom of the container 101, and the recessed position of the window 103 assure that the window 103 is positioned just below the surface of the water 124.

The detector 100 includes a system controller 102 which generates a pulsed trigger signal 104 that causes optical energy source 106 to generate a pulsed, broadband, excitation optical beam 108 that preferably includes UV light components. The excitation optical beam 108 is preferably collimated by lens 110 and then divided into optical signal 114 and sampled excitation optical beam 116 by beam splitter 112, such as a dichroic mirror. With regard to the present invention, beam splitters 112 and 122, each implemented as dichroic mirrors, reflect light components having wavelength components below a specific wavelength and is transparent to light having wavelength components above that wavelength. The portion of excitation optical beam 108 that is directed through beam splitter 112 is detected by photo detector 118. Photo detector 118 generates an output signal 120 responsive to the integrated intensity of signal 114 detected by the photo detector 118. The output signal 120 is received and processed by controller system 102.

Sampled excitation optical beam 116 is reflected by beam splitter 112 and directed to beam splitter 122 which reflects sampled excitation optical beam 116 through optical lens 123 and optically transparent window 103. Aqueous solution 124 is illuminated by sampled excitation optical beam 116. Aromatic compounds 125 present in oil samples that may be found in aqueous solution 124, fluoresce when illuminated by sampled excitation optical beam 116 to generate fluorescent optical signal 126 which is directed through window 103, lens 123, and beam splitter 122 to beam splitter 130. Beam splitter 130 divides optical signal 126 into signal 134, which passes through the beam splitter 130, and into optical signal 132. Optical signal 132 is focused by optical lens 136 and directed to photo detector 138. Photo detector 138 generates an output signal 140 responsive to the integrated intensity of signal 132 detected by the photo detector 138. The output signal 140 is received and processed by controller system 102.

Optical signal 134 is directed to beam splitter 135 which divides optical signal 134 into optical signal 142, directed through beam splitter 135, and into optical signal 144.

Optical signal 144 is focused by optical lens 146 onto photo detector 148. Photo detector 148 generates an output signal 150 responsive to the integrated intensity of signal 144 detected by photo detector 148. The output signal 150 is received and processed by controller system 102. Optical signal 142 is focused by optical lens 152 onto photo detector 154. Photo detector 154 generates an output signal 156 responsive to the integrated intensity of signal 142 detected by the photo detector 154. The output signal 156 is received and processed by controller system 102.

The generation of excitation optical beam 108 and detection of optical beams 114, 132, 144, and 156 by photo detectors 118, 138, 148, and 154, respectively, are synchronized in unison, or time gated by signal 104 to isolate signals of interest from background light. The controller system 102 may also store and/or process input signals 120, 140, 150, and 156, and generate an output signal 158, which may be provided to a display (not shown), representing the concentration of petroleum products and/or other chemical species that may be present in aqueous solution 124. The separation of optical signal 126 into optical beams 132, 144, and 156 wavelength components provides system 100 with the capability of performing spectral analysis of the signal 126 to discern the presence of polluting and/or non-polluting species 125 in aqueous solution 124.

By way of example, in the preferred embodiment: 1) beam splitter 112 may reflect optical energy having wavelengths less than about 315 nanometers (nm) and be transparent to optical energy having wavelengths greater than about 315 nm; 2) beam splitter 123 may reflect optical energy having wavelengths less than about 315 nanometers (nm) and be transparent to optical energy having wavelengths greater than about 315 nm; 3) mirror 130 may reflect optical energy having wavelengths less than about 400 nm, and be transparent to optical energy having wavelengths greater than about 400 nm; and 4) mirror 135 may reflect optical energy having wavelengths less than about 450 nm, and be transparent to optical energy having wavelengths greater than about 450 nm. Although detector 100 is shown to include four photo detectors, it is to be understood that detector 100 may be constructed with any suitable number of photo detectors and beam splitters. Furthermore, the beams splitters may be transparent to optical energy having wavelengths other than those specified above as required to suit the requirements of a particular application.

Figure 3:
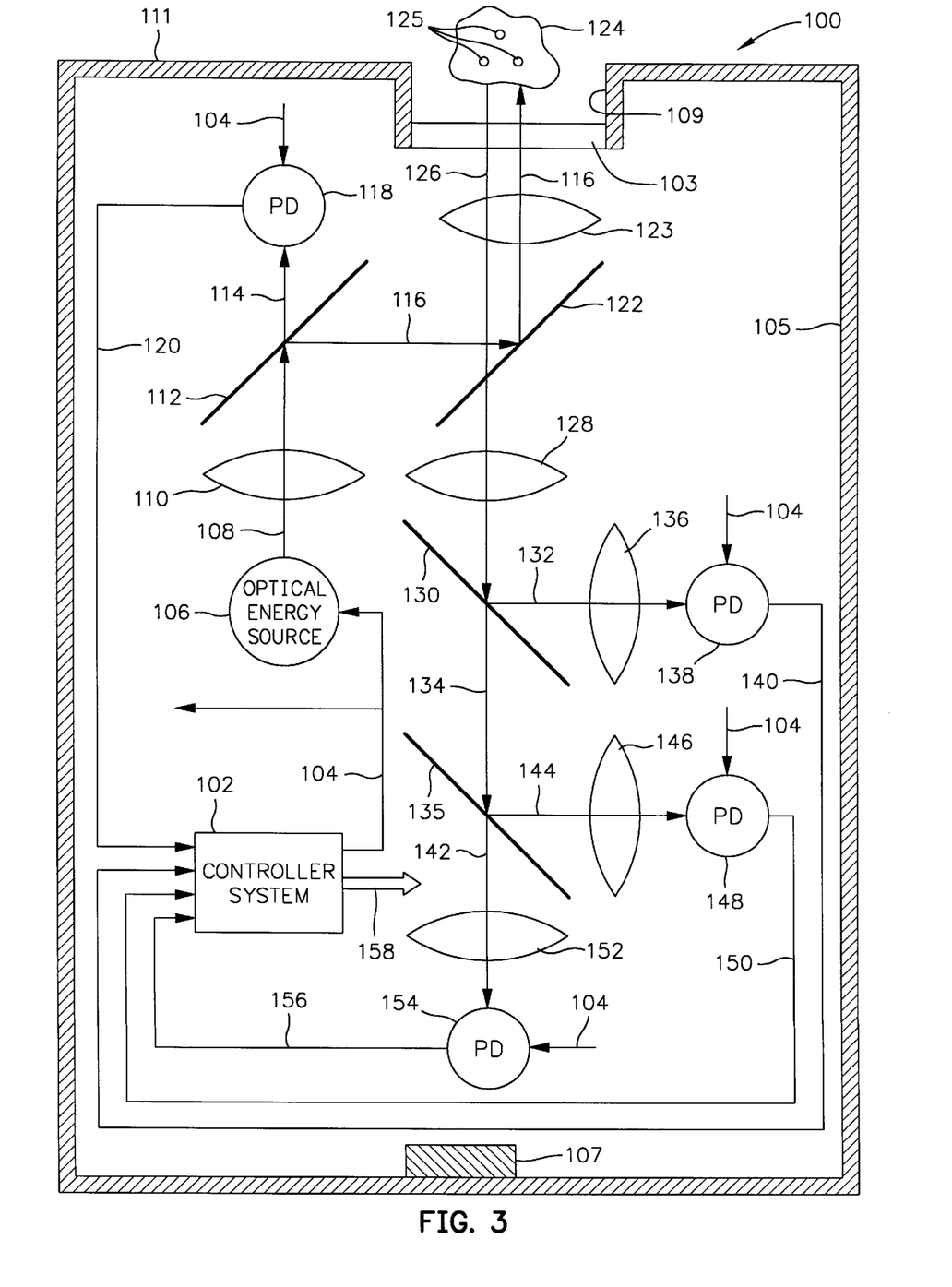
FIG. 3 is an example of another embodiment of the underwater spectroscopic detector of the present invention.
Figure 4A:
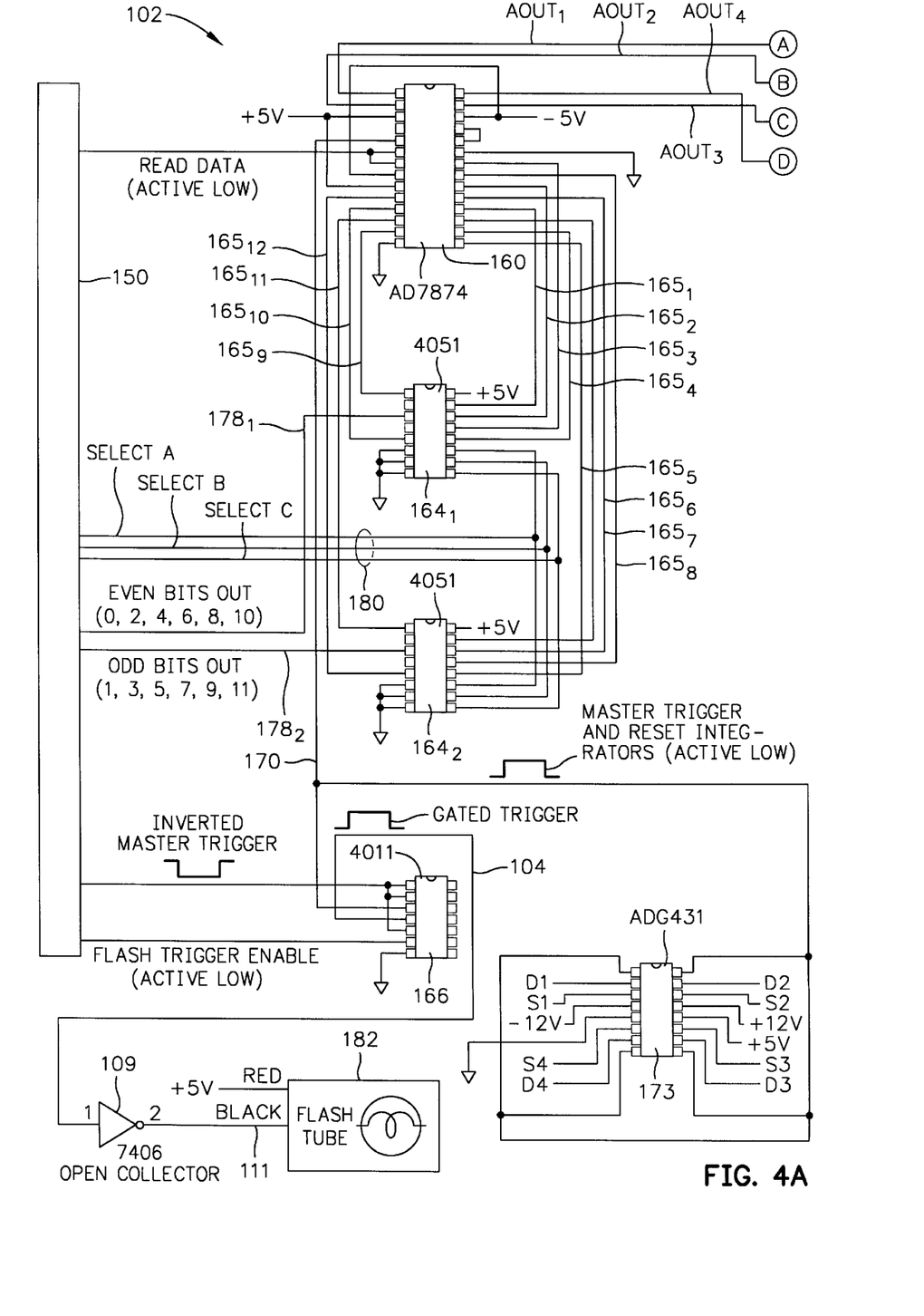
FIGS. 4A and 4B illustrates an example of an electrical circuit for implementing the photo detectors and controller system of FIG. 3.
Figure 4B:
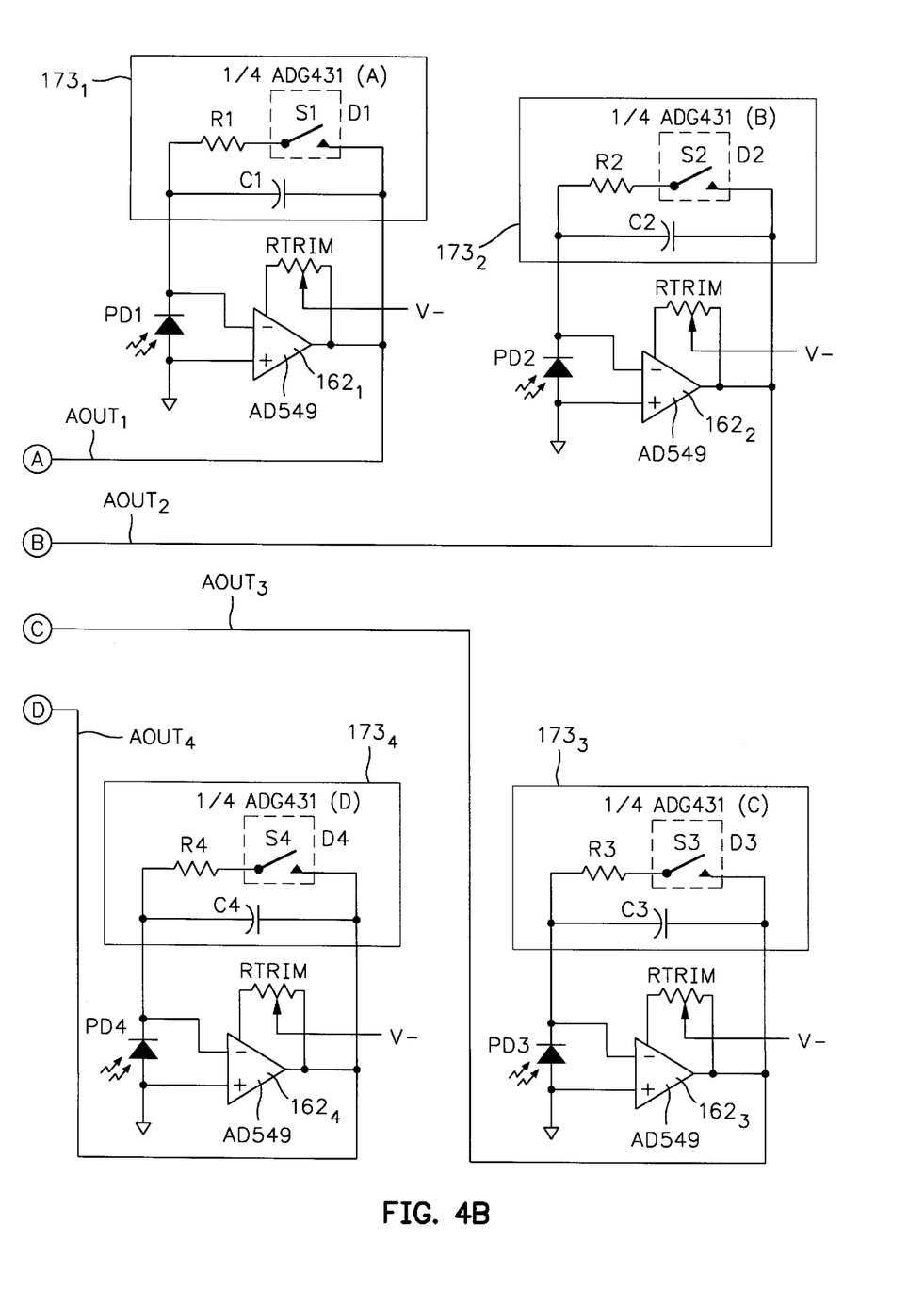
Figure 5:
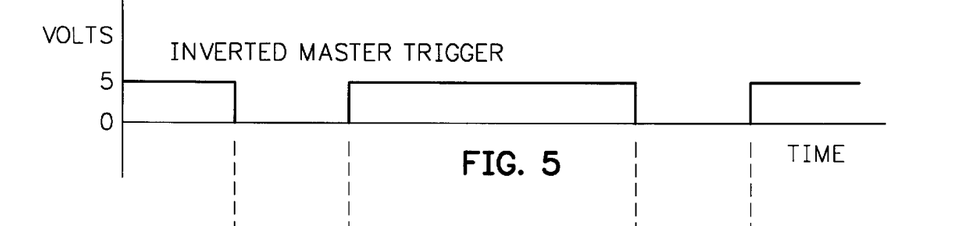
FIGS. 5–8 show relative timing diagrams for the Inverted Master Trigger signal, Master Trigger signal, Flash Trigger Enable signal, and Gated Trigger Signal.
Figure 6:
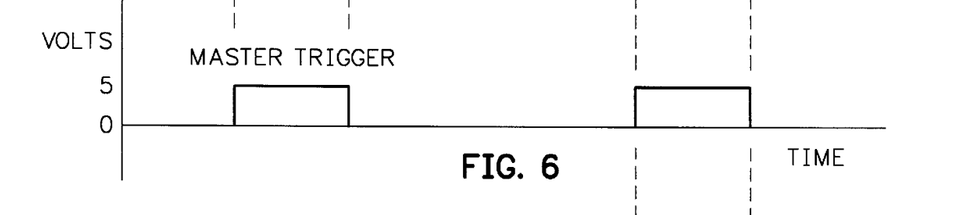
Figure 7:
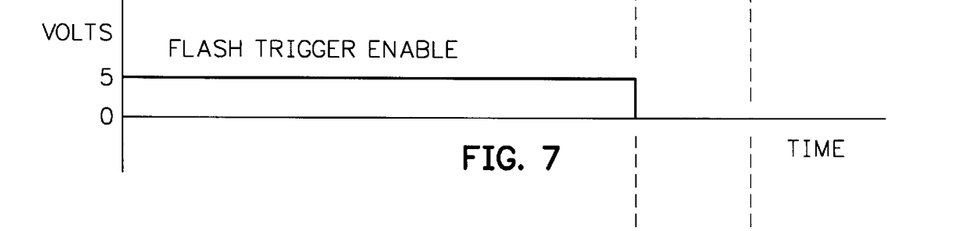
Figure 8:
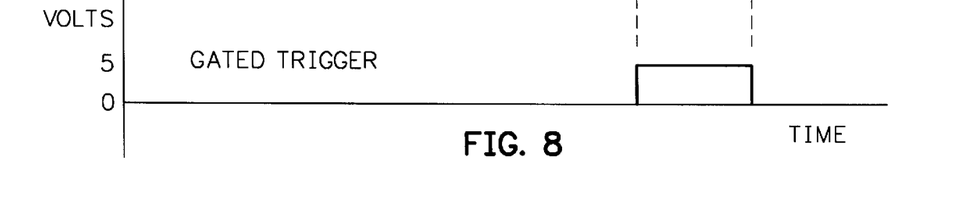

An example of an electrical circuit for implementing the photo detectors $PD_1$, $PD_2$, $PD_3$, and $PD_4$ and controller system 102 of FIG. 3 is described with reference to FIGS. 4A and 4B. As shown in FIGS. 4A and 4B, controller system 102 includes, inter alia, micro controller, 12-bit analog to digital (A/D) converter 160 having integrated 4-channel sample and hold circuits, op-amps $162_1$, $162_2$, $162_3$, and $162_4$ configured as resettable integrators, and multiplexers $164_1$, and $164_2$. An example of a suitable micro controller 150 is a DOMINO 52 micro controller based on the Intel 8052 micro processor. The integration functions of the inputs to op-amps $162_{1-4}$ are provided by capacitors $C_1$, $C_2$, $C_3$, and $C_4$ which are connected in parallel across reset switches $S_1$, $S_2$, $S_3$, and $S_4$, respectively. Reset switches $S_1$, $S_2$, $S_3$, and $S_4$, are connected in series with resistors $R_1$, $R_2$, $R_3$, and $R_4$ which dissipate charge stored by each of the capacitors. Capacitors $C_1$, $C_2$, $C_3$, and $C_4$, reset switches $S_1$, $S_2$, $S_3$, and $S_4$, and resistors $R_1$, $R_2$, $R_3$, $R_4$ collectively comprise reset switch circuits $173_1$, $173_2$, $173_3$, and $173_4$, respectively.

Photodiode's $PD_{1-4}$ are connected to op-amps $162_{1-4}$ (as for example, AD549) that are configured as resettable integrators. Op-amps $162_{1-4}$ are allowed to integrate only during the presence of trigger pulse 104, and are reset so that the op-amps $162_{1-4}$ have a "zero" output at all other times. A quad single pole, single throw analog switch circuit 166, such as Analog Device AGC431, provides the reset fuinction using single pole switches $S_1$, $S_2$, $S_3$, and $S_4$, connected in parallel with capacitors $C_1$, $C_2$, $C_3$, and $C_4$, respectively. Each of switches $S_{1-4}$ is controlled by a TTL level signal 170 so that all four switches $S_{1-4}$ are activated together. When the control line signal 170 has a logic low level, switches $S_{1-4}$ are closed, causing the output of op-amps $162_{1-4}$ to be near zero volts. When the logic level of signal 170 is high, switches $S_{1-4}$ are open whereupon the output signals of op-amps $162_{1-4}$ are each proportional to the integrated output of photo diodes $PD_{1-4}$, respectively.

The analog outputs AOUT1, AOUT2, AOUT3, and AOUT4 of op-amps $162_{1-4}$, respectively, are provided to four-channel analog to digital convertor (A/D) 160, which may be an Analog Devices AD7874 having four analog inputs, each with a sample and hold circuit. The inputs of A/D convertor 160 are all activated simultaneously by signal 170. Once the analog inputs to A/D convertor 160 are latched (when signal 170 line is a logic low), data conversion begins and four 12-bit digital values representing the outputs of op-amps $162_{1-4}$ are stored internally within the A/D convertor 160. After A/D conversion is completed, the first read signal (the READ DATA line is set low by micro controller 150) causes the 12-bit value representing the value on signal line $AOUT_1$ (channel 1) to be output in parallel on signal lines $165_{1-12}$ from A/D converter 160. The 12-bit value representing the value on signal line $AOUT_2$ (channel 2) is output in parallel on signal lines $165_{1-12}$ when the READ DATA line is cycled high, and then low again by micro controller 150. Thus, each data value stored in A/D converter 160 is read out in sequence on signal lines $165_{1-12}$, respectively, as the READ DATA line is alternately toggled high then low by the micro controller 150. The micro controller 150, implemented in FIGS. 4A and 4B, has insufficient inputs to read an entire 12-bit word in at once so the digital output signals $165_{1-12}$ from A/D convertor 160 are multiplexed through two 8:1 multiplexers $164_{1-2}$. Output signals $165_{1, 3, 5, 7, 9, and 11}$ of A/D converter 160 are provided to multiplexer $164_1$, and output signals $165_{2, 4, 6, 8, 10, and 12}$ of A/D converter 160 are provided to multiplexer $164_2$. The output signal $178_1$ of multiplexer $164_1$ is provided as an input to micro controller 150. Similarly, the output signal $178_2$ of multiplexer $164_2$ is provided as an input to micro controller 150. A 3-bit address provided by the micro controller 150 on signal lines 180 determines which of the data on the 12 data output signals $165_{1-8}$ are selected to be input to the micro controller 150 via one of the multiplexers $162_1$ or $162_2$. The even bits (0, 2, 4, 6, 8, 10) from the A/D convertor 160 are connected to multiplexer $164_1$ via signal lines $165_{1, 3, 5, 7, 9, and 11}$ and the odd bits (1, 3, 5, 7, 9, 11) from the A/D convertor 160 are connected to multiplexer $164_2$ via signal lines $165_{2, 4, 6, 8, 10, and 12}$. The digital output of A/D convertor 160 is read into the micro controller 150, two bits at a time, via multiplexers $164_{1-2}$ by placing the appropriate sequence of mux addresses on the mux select lines ("Select A", "Select B", "Select C") 180 as follows:

| Select<br>CBA | Data Bits<br>Selected |
|---|---|
| 000 | 0, 1 |
| 001 | 2, 3 |
| 010 | 4, 5 |
| 011 | 6, 7 |
| 100 | 8, 9 |
| 101 | 10, 11 |

In the sequence of operation of controller system 102 events during a sample period is described as follows with reference to FIGS. 5–8, micro controller 150 sets the signal line "Inverted Master Trigger" to a logic low. Because micro controller 150 defaults to a high state on the I/O pins, it was preferred to use a negative going pulse for a trigger signal referred to as the Inverted Master Trigger signal. The "Master Trigger" signal is provided to A/D convertor 160 and to the switch controls of reset circuits $173_{1-4}$. When the "Master Trigger" signal is high, A/D convertor 160 samples the analog input voltages $AOUT_{1-4}$ continuously received from op-amps $162_{1-4}$, representing the integrated output of photo diodes $PD_{1-4}$, respectively. On the falling edge of the "Master Trigger" signal, A/D convertor 160 latches the input voltages $AOUT_{1-4}$ into its internal sample and hold and begins the A/D conversion process. Then, the op-amps $162_{1-4}$ are reset (held in a low voltage output) when the Master Trigger signal is low. Sufficient delay in the response times of A/D convertor 160 and reset circuit 173 (such as a AGC431) assure that voltage signals $AOUT_{1-4}$ are latched by the A/D convertor 160 before they are reset. If Flash Trigger Enable signal is low, then the flash tube 182 will flash during the period that "Master Trigger" is high. Signal 104 is conditioned by buffer 109 which generates signal 111 having sufficient power to trigger flash tube 182.

A software time delay implemented by micro controller 150 provides, by way of example, a 33 ms delay between flashes. The four 12-bit digital values of signal $178_{1-2}$ are read in by micro controller 150 and stored in RAM for post processing. Timing diagrams for the Inverted Master Trigger signal, Master Trigger signal, Flash Trigger Enable signal, and Gated Trigger Signal are illustrated in FIGS. 5–8.

Figure 9:
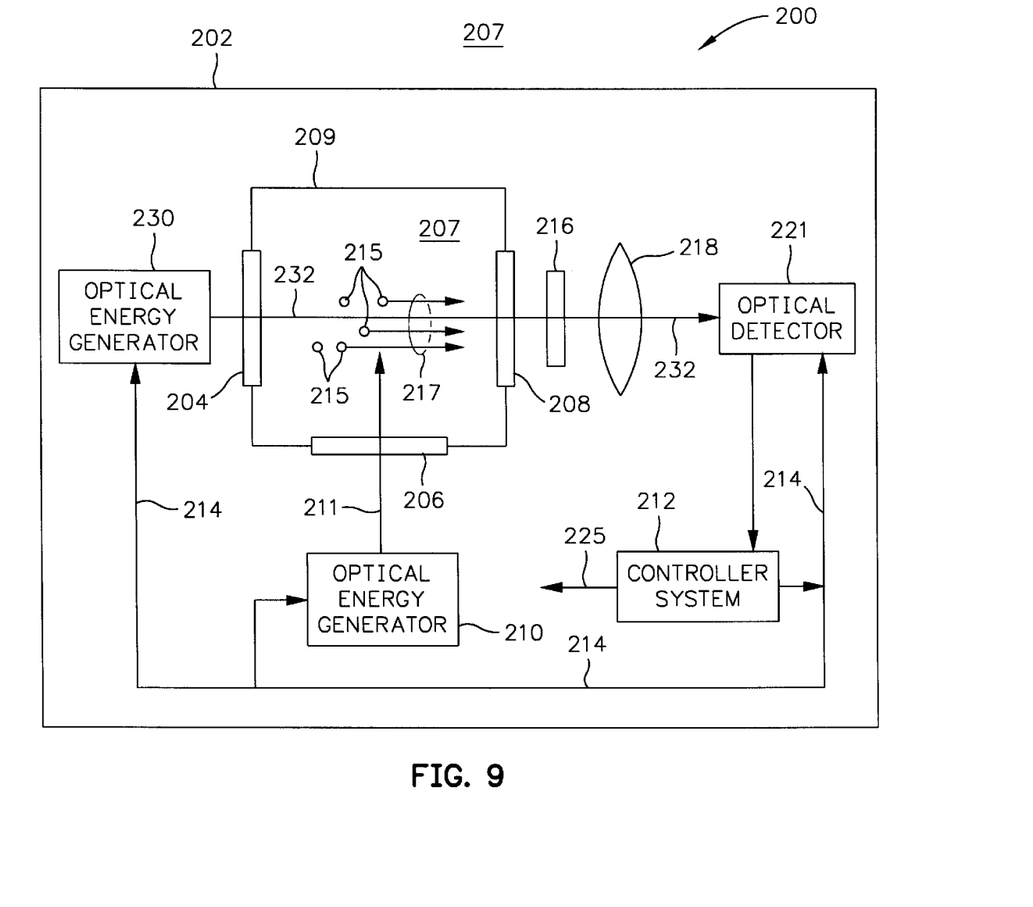
FIG. 9 is a block diagram of another embodiment of an underwater spectroscopic detector embodying various features of the present invention.

Referring to FIG. 9, there is shown another embodiment of an underwater spectroscopic detector embodying various features of the present invention. As shown in FIG. 9, detector 200 is preferably encased in a waterproof structure 202 which may have positive, neutral, or negative buoyancy, to suit the requirements of a particular application. By way of example, the structure 202 is described and illustrated as having positive buoyancy. Three optically transparent windows 204, 206, and 208 are mounted in a recessed region 209 in fluid communication with an aquatic environment 207. The recessed region 209 is formed in the top of structure 202 so that the windows 204, 206, and 208 float just below the surface of the aquatic environment 207. Optical windows 204 and 208 face each other, and are generally perpendicular to window 206. The detector 200 includes an optical energy generator 210 mounted in structure 202 which generates optical energy beam 211, having ultraviolet light components. The optical energy beam 211 is directed through window 206 into the aquatic environment 207 present in recessed region 209. Chemical species 215, such as aromatic compounds and/or other that may be present in the aquatic environment 207 which are to be detected generally fluoresce by generating light signals 217 having wavelengths greater than those of excitation optical beam 108 when irradiated by optical beam 211 having ultraviolet (UV) light components for inhibiting the growth of biological organisms on window 206. The ultraviolet components of optical signal 211 significantly also inhibit or prevent biological organisms from forming on window 206. Fluorescent light signals 217 that radiate through window 208, optical filter 216, and optional optical lens 218 are detected by optical detector 221. Optical filter 216 is preferably transparent to optical signals 217 having wavelengths of interest (greater than about 315 nm), but which greatly attenuates optical signals such as excitation optical beam 211 having wavelengths less than about 315 nm. The optical detector 221 generates an output signal 223 responsive to the integrated intensity of light signals 217 that is provided to controller system 212 for suitable analysis. The controller system 212 then generates an output signal 225 that represents the intensity of the optical signals 217 detected by the optical detector 221.

System 200 further includes a second optical generator 230 which generates optical signal 232 having ultraviolet light components. Optical signal 232 is directed through windows 204 and irradiates window 208 to inhibit or prevent biological organisms from forming on window 208. Optical signal 232 is preferably significantly attenuated by filter 216 so that the intensities any components of optical signal 232 that irradiate optical detector 221 are not significant with respect to the intensity of optical signals 217 detected by optical detector 221.

Controller system 212 generates control signals 214 that direct optical energy generators 210 and 230 to generate optical beams 211 and 232, respectively, each as a pulsed beam at a pulse frequency, for example, of about 30 Hz and having a pulse period of about 200 ms. Control signals 214 also synchronize the detection of optical signals 217 with the generation of optical beam 211 to isolate the signal of interest (optical signals 217) from background light, such as sunlight and minimizes thermal noise.

In the preferred embodiment, optical generators 210 and 230 generates optical energy having components in the ultraviolet light range, generally having wavelengths of about 150 to 400 nanometers. Ultraviolet light inhibit or prevents, or at least minimizes the formation of biological organisms on the windows 204, 206, and 208, with the attendant benefit of reducing maintenance and service requirements for the detector 200. The intensity of light signals 211 and 232 should be sufficient to inhibit or prevent the accumulation of biological organisms on the windows 204, 206, and 208. The windows are preferably made of an optically transparent material such as quartz, glass, or sapphire.

Figure 10:
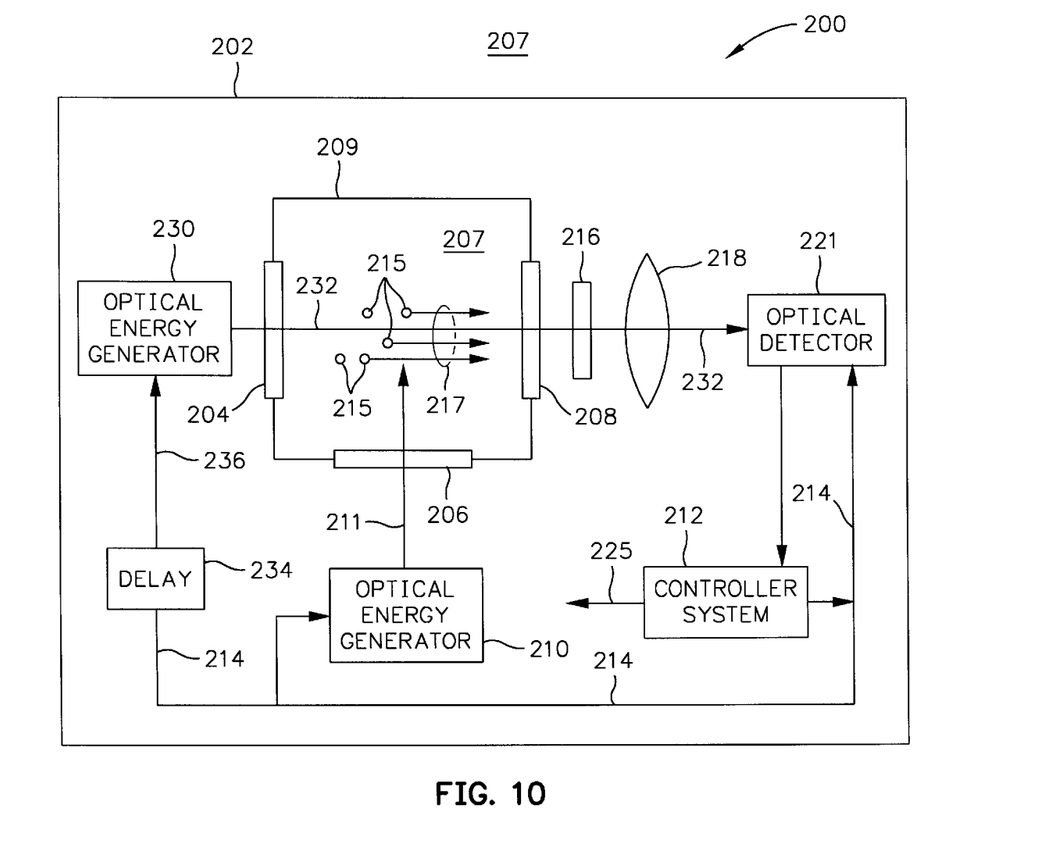
FIG. 10 is a block diagram of another embodiment of an underwater spectroscopic detector embodying various features of the present invention.

As shown in FIG. 10, detector 200 may further include a delay circuit 234 which receives the pulsed signals 214 from controller system 212 and generates an output signal 236 which is out of phase with signal 214. The output signal 234 is used to drive the optical energy generator 230 so that the optical signal 232 is not present during the time interval when optical signal 211 is present. Therefore, optical detector 221 is capable of detecting optical signals 217 only when optical signal 232 is not present, thereby obviating the need for optical filter 216 and reducing the signal to noise ratio of optical detector 221.

Obviously, many modifications and variations of the present invention are possible in light of the above teachings. It is therefore to be understood that within the scope of the appended claims, the invention may be practiced otherwise than as specifically described.

We claim:

1. A spectroscopic detector, comprising:

a container having an optically transparent window;

a beam splitter mounted in said container;

an optical energy generator mounted in said container for directing an excitation optical energy beam through said beam splitter and said window for irradiating chemical species in an aqueous environment so that said chemical species generate a fluorescent optical energy beam; and an optical detector for generating an output signal in response to detecting said fluorescent optical energy beam received in said container through said window and reflected to said optical detector by said beam splitter.

2. The spectroscopic detector of claim 1 further including a controller which directs said optical energy generator to generate said excitation optical energy beam as a pulsed beam.

3. The spectroscopic detector of claim 2 wherein said controller directs said optical detector to detect said fluorescent optical energy beam synchronous with generation of said excitation optical energy beam by said optical energy generator.

4. The spectroscopic detector of claim 1 wherein said optical detector includes a charge coupled device.

5. The spectroscopic detector of claim 1 wherein said optical detector includes a photo multiplier tube.

6. The spectroscopic detector of claim 1 wherein said optical detector includes a photo diode.

7. The spectroscopic detector of claim 1 wherein said beam splitter is a dichroic mirror.

8. The spectroscopic detector of claim 1 wherein said excitation optical energy beam includes optical components having wavelengths less than about 400 nanometers.

9. The spectroscopic detector of claim 1 optical energy generator is a flashlamp.

10. The spectroscopic detector of claim 1 wherein said optical energy detector is a laser.

11. The spectroscopic detector of claim 1 wherein said beam splitter is a dichroic mirror.

12. The spectroscopic detector of claim 1 wherein said container is water proof.

13. The spectroscopic detector of claim 1 wherein said container has positive buoyancy in an aquatic environment.

14. The spectroscopic detector of claim 1 wherein said container has neutral buoyancy in an aquatic environment.

15. The spectroscopic detector of claim 1 wherein said container has negative buoyancy in an aquatic environment.

16. A spectroscopic detector, comprising:

a container having an optically transparent window;

a beam splitter mounted in said container;

an optical energy generator mounted in said container for generating a first optical energy beam which is directed through said beam splitter and said window for irradiating chemical species in an aqueous environment so that said chemical species generate a fluorescent optical energy beam, wherein said first optical beam inhibits formation of biological organisms on said window; and an optical detector for generating an output signal in response to detecting said fluorescent optical energy beam received in said container through said window and reflected by said beam splitter to said optical detector.

17. The spectroscopic detector of claim 16 wherein said first optical energy beam includes optical energy having wavelengths less than about 315 nanometers.

18. A spectroscopic detector, comprising:

a structure having a recessed region;

a first optical window mounted in said recessed region;

a second optical window mounted in said recessed region so as to face said first optical window;

a third optical window mounted in said recessed region generally perpendicular to said first and second windows;

a first optical energy generator for generating first optical energy beam pulses having ultraviolet light components, and which are directed through said third optical window;

a second optical energy generator for generating a second optical energy beam having ultraviolet light components and which is directed through said first and second optical windows;

an optical detector for generating an output signal in response to detecting an optical signal through said second optical window concurrent with said first optical energy beam pulses, where said optical signal is generated by irradiating chemical species in said recessed region with said first optical energy beam; and a controller for directing said first and second optical energy generators to generate said first and second optical energy beams, respectively.

19. The spectroscopic detector of claim 18 further including an optical lens for focusing said optical signal onto said optical detector.

20. The spectroscopic detector of claim 18 wherein said second optical energy beam is pulsed in substantial synchroneity with said first optical energy beam pulses.

21. The spectroscopic detector of claim 18 further including an optical filter interposed between said second optical window and said optical detector for attenuating said second optical energy beam.

22. The spectroscopic detector of claim 18 wherein said controller alternately directs said first and second optical energy generators to generate said first and second optical energy beams, respectively.

23. The spectroscopic detector of claim 18 wherein said first optical energy beam inhibits formation of biological organisms on said third optical window.

24. The spectroscopic detector of claim 18 wherein said second optical energy beam inhibits formation of biological organisms on said first and second optical windows.

25. The spectroscopic detector of claim 18 wherein said second optical energy beam is pulsed between said first optical energy beam pulses.

* * * * *